United States Patent [19]

Winkler et al.

[11] Patent Number: 4,526,913

[45] Date of Patent: Jul. 2, 1985

[54] DIMER POLYMERIC COATING SELECTIVELY STRIPPABLE AS COHESIVE FILM

[75] Inventors: David S. Winkler, Wooster, Ohio; Jeffrey H. Diamond, Palm Beach, Fla.

[73] Assignee: J. H. Diamond Company, Lake Worth, Fla.

[21] Appl. No.: 570,336

[22] Filed: Jan. 13, 1984

[51] Int. Cl.$^3$ .................. C08G 18/10; C08L 1/18; C08L 75/04

[52] U.S. Cl. .................. 524/31; 524/32; 524/33; 525/28; 428/423.4; 428/532; 424/32; 424/33; 424/34; 424/35

[58] Field of Search ........ 524/31, 32, 33; 525/28; 428/423.1, 423.4, 532; 424/32, 33, 34, 35

[56] References Cited

U.S. PATENT DOCUMENTS

| | | | |
|---|---|---|---|
| 2,949,445 | 8/1960 | Blake | 525/327.3 |
| 3,475,356 | 10/1969 | Davis et al. | 524/39 |
| 3,583,932 | 6/1971 | Benton et al. | 428/441 |
| 3,816,168 | 6/1974 | Lewis et al. | 427/389 |
| 3,834,936 | 9/1974 | Schroer et al. | 427/389 |
| 3,893,978 | 7/1975 | Cleur et al. | 528/45 |
| 3,896,014 | 7/1975 | Rosenberg | 204/159.23 |
| 3,928,113 | 12/1975 | Rosenberg | 156/344 |
| 3,932,342 | 1/1976 | Nagata et al. | 524/441 |
| 3,952,032 | 4/1976 | Vrancken et al. | 260/404.8 |
| 3,987,223 | 10/1976 | Wagner et al. | 427/389 |
| 4,028,322 | 6/1977 | Mory | 106/288 Q |
| 4,029,847 | 6/1977 | Imagawa et al. | 524/31 |
| 4,049,871 | 9/1977 | Ogawa et al. | 428/425 |
| 4,067,834 | 1/1978 | Olstowski | 524/773 |
| 4,071,639 | 1/1978 | Palmer et al. | 427/156 |
| 4,082,710 | 4/1978 | Vrancken et al. | 204/159.14 |
| 4,096,101 | 6/1978 | Blahak et al. | 521/136 |
| 4,156,064 | 5/1979 | Falkenstein et al. | 524/31 |
| 4,169,167 | 9/1979 | McDowell | 427/54 |
| 4,171,361 | 10/1979 | Dillard et al. | 424/246 |
| 4,180,645 | 12/1979 | Emmons et al. | 528/73 |
| 4,198,200 | 4/1980 | Fonda et al. | 431/360 |
| 4,218,294 | 8/1980 | Brack | 204/159.13 |
| 4,225,489 | 9/1980 | Rolf et al. | 428/411 |
| 4,235,766 | 11/1980 | Kuijer | 525/131 |
| 4,271,217 | 6/1981 | Tanaka et al. | 428/96 |
| 4,288,479 | 9/1981 | Brack | 428/40 |
| 4,299,868 | 11/1981 | Berndt et al. | 427/389.9 |
| 4,303,696 | 12/1981 | Brack | 427/44 |
| 4,307,224 | 12/1981 | Rogier | 528/272 |
| 4,317,894 | 3/1982 | Lewarchik et al. | 525/455 |
| 4,336,171 | 6/1982 | Kohlstadt et al. | 524/510 |
| 4,368,238 | 1/1983 | Somezawa et al. | 428/413 |
| 4,404,347 | 9/1983 | Nakamura et al. | 527/300 |
| 4,413,079 | 11/1983 | Disteldorf et al. | 524/169 |
| 4,413,111 | 11/1983 | Markusch et al. | 528/59 |
| 4,423,179 | 12/1983 | Guagliardo | 524/539 |
| 4,442,280 | 4/1984 | Grogler et al. | 528/54 |

OTHER PUBLICATIONS

Journal of Elastomers and Plastics, vol. 7 (Jan. 1975), pp. 35–46, by Howard J. Stephens, Jeffrey W. Saracsan, Deepak V. Vaidya and David S. Winkler.

Henkel Corporation Literature, DDI 1410 Diisocyanate, pp. 1, 2, 6 and 9 along with a page of charted out reactions.

Monsanto Industrial Chemicals Co. Literature, Santolite MHP, toluenesulfonamideformaldehyde resin, 4 pages.

*Primary Examiner*—John Kight
*Assistant Examiner*—Nathan M. Nutter
*Attorney, Agent, or Firm*—Pollock, Vande Sande & Priddy

[57] ABSTRACT

A polymeric coating composition containing nitrocellulose, an acrylate copolymer, a prepolymer from a dimer diisocyanate and a difunctional monomer with an active hydrogen in each group, and a diamine. Solvents may include isopropyl alcohol, ethyl acetate, and toluene. Optionally there may be included a second copolymer from a sulfinamide and formaldehyde and/or a plasticizer. A dried coating from this composition is selectively strippable from a substrate as a cohesive film upon application of a remover solution containing acetone, isopropyl alcohol and water.

39 Claims, No Drawings

DIMER POLYMERIC COATING SELECTIVELY STRIPPABLE AS COHESIVE FILM

TECHNICAL FIELD

The present invention is concerned with polymeric compositions that are useful in providing protective and/or decorative coatings on a substrate. More particularly, the present invention is concerned with polymeric compositions that are capable of being applied as a liquid and cured by drying in air at ambient conditions to provide a tough, relatively hard coating which has strong adhesion to the substrate, does not dissolve in water and in many organic solvents and is resistant to swelling in water and in many organic solvents, but can be removed readily from the substrate as a cohesive film upon treatment with a select remover solution. These compositions are especially useful as decorative nail polish or to protect metal components from corrosive liquids or vapors.

BACKGROUND OF THE INVENTION

Compositions, to be suitable as decorative or protective coatings, should provide coatings having good adhesion characteristics in the presence of water and/or organic solvents. In order to provide such adhesion, the cured coating needs to be resistant to both solvation and swelling when in contact with such solvents. On the other hand, the cured coating needs to be easily removable when it is desired to change the decorative coating or place the protected component into use.

One way to remove a decorative or protective coating is to treat it with a solvent for the coating material. The solvated coating then becomes fluid and can be wiped off as a paste-like material. However, this removal technique can be quite messy. For example, when fingernail polish is treated with the usual polish remover, the solvated coating becomes a fluid mass that must be wiped off with an absorbent material. Wiping away this fluid mass, which usually contains color pigments, is very often messy and may leave portions of the solvated coating smeared over adjacent surfaces and lodged in finger or toe crevices. The solvated coating can also be accidentally transferred to other surfaces, such as an article of clothing, from which it may be quite difficult to remove.

Some of the coating compositions of the prior art can be brushed or sprayed onto a surface and upon drying, form a film that can be removed by peeling the film from the surface. Such films have relative poor adhesion characteristics because they rely on removal by a mechanical peeling step alone. Thus, easily peelable films in the past have had the disadvantage of being relatively easily detached by moisture and/or by organic solvents so that they tend to come loose prematurely from the surface of a substrate. Such films may also come loose from the substrate because they do not adhere well to certain materials, such as plastics or other resins or painted surfaces, or because they are actually attacked by the material of the substrate itself. In other words, mechanically peelable coatings are often held on the substrate surface by relatively low levels of interfacial forces. It is therefore desirable that coatings removable as strippable films be easily separated from the substrate surface when desired but otherwise be strongly adhered to the substrate surface by high levels of interfacial forces.

Strippable films are also useful for stenciling the surface of a substrate such as wood, metal or plastic or the painted surface of such a substrate. In stenciling, the substrate surface is sprayed with a coating composition that is dried to form a strippable film coating and the pattern desired is cut in this film coating. The unwanted portions of the film are then stripped from the substrate surface to the leave the stencil pattern behind. The stripped portions of the substrate surface are then coated with ink or a suitable paint. After the ink or paint has dried in the desired pattern, the remainder of the strippable film is removed, leaving the desired pattern on the substrate surface. The advantage of a peelable stencil coating is that contamination or smearing of the dried ink or paint by a solvated coating is avoided.

It would therefore be highly desirable for a strippable coating film to adhere to the surface of the substrate with a high level of interfacial forces during the time that decoration and/or protection is desired, and with a low level of interfacial forces when the substrate surface is to be exposed by stripping off the strippable coating. It is also highly desirable that the coating be removable as a single piece of cohesive film. Furthermore, during removal none of the materials in the film, such as color pigments, should exude or bleed out of the film because such released materials could smear to adjacent surfaces and could be transferred to still other surfaces, thereby creating a mess. It is also desirable that such materials not exude or bleed out of the composition while it is in use for the same reasons. In addition, loss of such materials could change the color or other characteristics of the adhered film.

Accordingly, it is readily apparent that a coating composition, to be suitable for the above purposes, must possess a number of critical properties and characteristics which are quite difficult to achieve. This problem is made more acute when an object also is to formulate a strippable coating composition at relatively low cost.

DISCLOSURE OF THE INVENTION

It is an object of the present invention to provide a polymeric coating which adheres to the surface of a substrate with a high level of interfacial forces which are maintained in the presence of water and many organic solvents but which is reduced sufficiently to permit removal of the coating as a cohesive film by the application of a select solvent. The coating provided by the compositions disclosed has a high level of adherence to a wide variety of surfaces, such as unpainted or painted wood, glass, plastic, and metal. The composition provides a flexible, tough, strongly cohesive and relatively hard coating. The coating is suitable for decorative purposes and/or for protecting a substrate surface against corrosion and against scratching and other marring during packaging and shipment. Since the cured film is not adversely affected by moisture and many organic solvents, the invention is particularly useful as a protective coating for pipes and other metal parts to prevent contact between a corrosive environment and the metal substrate surface. Another advantage of the cured coating of the present invention is that the integrity of the coating is maintained during its removal as a cohesive film with the select remover solution. The invention thus provides a neat and clean way to remove a colored coating from a substrate surface. The coating can be easily stripped from a substrate surface without creating a mess by applying the select remover solution. Except for the remover solution, the coating not only resists solvent attack but provides a solvent-resistant bond to the substrate surface.

The flexible, tough coating provided by the invention is especially useful as a fingernail or toenail polish which can be easily removed as a cohesive film when it is desired to change the color of the applied coating. The coating, when cured, is adequately flexible and tough to prevent chipping of the coating material, i.e., they have a high degree of chip resistance. At the same time, the cured coating may provide a hard, high gloss appearance.

The present invention is concerned with a strippable cohesive coating from:
(a) an acrylate copolymer and/or nitrocellulose;
(b) a prepolymer from a dimer diisocyanate and a dihydric alcohol and/or another monomer with two or more functional groups each having an active hydrogen; and,
(c) a diamine.

Nitrocellulose and a solvent for the nitrocellulose may be substituted for the acrylate copolymer and its solvent, but a preferred embodiment employs both the copolymer and the nitrocellulose. The present invention is also concerned with a select remover solution which is specific to the coating composition to be removed, the cured coating composition being resistant to solvation, swelling and/or removal by other organic solvents and water.

A composition suitable for preparation of the above strippable cohesive coating further includes a solvent for the acrylate copolymer and a solvent for the prepolymer which may be the same as or different from the solvent for the acrylate copolymer. Where the film forming composition includes nitrocellulose, a solvent for the nitrocellulose is also included.

The polymer compositions of the present invention contain a prepolymer from a dimer diisocyanate and a plural functional monomer having an active hydrogen in each functional group. This monomer is preferably a dihydric or polyhydric alcohol. Other difunctional monomers with active hydrogen in each group may be substituted for the alcohol in making up the prepolymer. Such difunctional monomers include other hydroxyl compounds and also compounds having dual thiol, amino and/or carbamate groups.

The dimer diisocyanate is preferably an aliphatic diisocyanate based on a dimerized fatty acid containing 36 carbon atoms. The prepolymer of the invention may be prepared without the use of solvents according to the procedures described in the article entitled "Room Temperature Cured Glycol/Dimer Diisocyanate Urethane Elastomers", published in Vol. 7 (January 1975), page 35, of the *Journal of Elastomers and Plastics*, the contents of which are incorporated herein by reference. Although the prepolymer may be added to the coating composition without prior dilution and/or dissolution, it is preferably added as a 50% by weight solution in toluene.

The use of a dimer diisocyanate avoids the need for masking the NCO groups. The preferred dimer diisocyanate has the following structure:

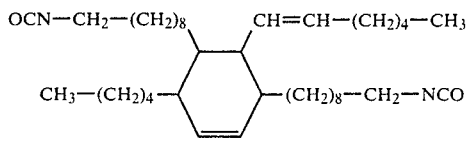

The above dimer diisocyanate is available as DDI 1410 from the Henkel Corporation of Minneapolis, Minn., and is preferred because of its water insensitivity, controllable reactivity, and low toxicity when compared to other aliphatic diisocyanates. The dimer diisocyanate preferably contains 13.6% to 14.3% by weight of NCO groups and has a molecular weight of about 600 prior to reacting with a dihydric alcohol to produce the prepolymer.

The dihydric alcohol can be a low molecular weight glycol, such as trimethylene or triethylene glycol, the latter being preferred. 2 moles of the dimer diisocyanate are reacted with 1 mole of the dihydric alcohol to produce 1 mole of the prepolymer. This prepolymer preferably has an NCO content of about 6.0% by weight and is preferably used in the form of a 50% by weight solution in toluene. More preferably, the alcohol is a mixture of 0.9 moles triethylene glycol and 0.1 moles glycerol. Although triethylene glycol may be used alone, it is preferred to include about a one/tenth proportion of glycerol relative to the glycol. The use of a small quantity of this trihydric alcohol is believed to slow down extension of the prepolymer with the diamine so as to permit more cross-linking between the prepolymer and the other polymeric ingredients.

The compositions of the present invention also contain a short chain aliphatic or aromatic diamine, preferably in the amount of 1.8 moles of diamine per mole of prepolymer. Use of 1.8 moles of diamine per mole of prepolymer leaves sufficient NCO terminal groups to react with the urea linkages present after the extension reaction. This amount of diamine also is chosen so that all of it is ultimately tied up in the polymeric structure so as to eliminate diamine toxicity. A preferred diamine is hexamethylene diamine (HMDA). Other suitable diamines include 1,3-diaminopropane (DAP), 1,4-cyclohexanebis-methylamine (CBMA), 4,4'-methylene-bis-(2-chloroaniline) (MOCA), p,p'-Methylenedianiline (MDA), and 2,4-toluenediamine (TDA).

The compositions of the present invention also may contain an acrylate copolymer, preferably a copolymer from methyl methacrylate and butyl methacrylate. This latter copolymer is available as Acryloid B-66 from Rohm & Haas Company of Cleveland, Ohio. Acryloid B-66 is a 50% by weight solution of this copolymer in xylene. A preferred solvent for both the acrylate copolymer and the prepolymer is toluene such that the xylene in the premixed copolymer solution could be replaced by toluene. Other suitable acrylate copolymers include those from methyl methacrylate and ethyl acrylate and from butyl methacrylate and ethyl acrylate.

The compositions of the present invention also may contain nitrocellulose and a solvent for the nitrocellulose. The solvent is preferably a mixture of isopropyl alcohol and ethyl acetate, the ethyl acetate having a high solubility for nitrocellulose and the isopropyl alcohol serving primarily as a diluent. A solvated nitrocellulose available from Hercules, Inc., of Wilmington, Del., contains about 70% by weight nitrocellulose in isopropyl alcohol. This is preferably diluted further with isopropyl alcohol and used as about a 35% by weight nitrocellulose solution. A composition suitable for preparation of a strippable cohesive coating may be provided by either nitrocellulose and its solvent or the acrylate copolymer and its solvent. However, the combination of the nitrocellulose component with the acrylate copolymer component yields a much superior product for many applications, particularly for providing a high gloss nail polish.

The compositions of the present invention also may contain a second copolymer to improve substrate adhesion, preferably from a toluene sulfonamide and formaldehyde. A preferred copolymer of this type is available as Santolite MHP Resin or Santolite MS-80 resin from Monsanto Industrial Chemicals Company of St. Louis, Mo. The MHP Resin is supplied as a solid while the MS-80 resin is supplied as a solution of 80% by weight resin in butyl acetate. The MS-80 resin is preferred because of the time required to dissolve the MHP resin in a solvent, such as butyl acetate. This copolymer is optional but is preferred as it improves the adhesion between the film and many substrate materials.

Another optional but preferred ingredient of the composition is a plasticizer, preferably dibutyl phthalate. Other suitable plasticizers include dioctyl phthalate, tributyl aconitate, acetyl tributyl citrate, dioctyl phenyl phosphate, triethylene glycol di-2-ethylbutyrate, tributyl tricarballylate, and dibutyl sebacate.

In order to increase the rate of reaction between the prepolymer, the copolymer and the nitrocellulose, a catalyst may be used such as lead, tin or zinc octoate and/or higher temperatures may be used. However, such reaction rate assists may lead to excessive viscosity or nonuniform mixtures and are not preferred.

The invention also concerns the order of mixing the ingredients to prepare a coating composition for application to a substrate surface. Where the acrylate copolymer is used without nitrocellulose, the copolymer is first mixed uniformly with its solvent, then the plasticizer and second copolymer (if used) are together mixed uniformly with the solvated copolymer. The prepolymer is then mixed uniformly with the copolymer mixture. The last ingredient added is the diamine. The preferred solvent for the acrylate copolymer is toluene which also serves as a solvent for the prepolymer. If the solvent for the acrylate copolymer is not a good solvent for the prepolymer, such as xylene, the prepolymer is preferably premixed with its own solvent, such as toluene.

In the above mixing sequence, nitrocellulose can be substituted for the acrylate copolymer. The nitrocellulose ingredient is preferably premixed with a diluent, such as isopropyl alcohol, and then with a true solvent, such as ethyl acetate. The order of adding the alcohol versus the acetate is not critical. The plasticizer (if used), the second copolymer (if used), and the prepolymer are then added separately and each mixed in uniformly, the order of mixing in these ingredients not being critical. Alternatively, the plasticizer and second copolymer may be added together, either before or after the prepolymer. Since neither isopropyl alcohol nor ethyl acetate are good solvents for the prepolymer, toluene is preferably used as a solvent for the prepolymer in this combination of ingredients. After a uniform mixture of these ingredients is obtained, the diamine is added last.

In a preferred composition for nail polish, both the acrylate copolymer and the nitrocellulose ingredients are used. In this embodiment, the mixing sequence is the same as for nitrocellulose alone through the addition of the diamine. The acrylate copolymer is then added last and mixed uniformly into the final composition. Although the acrylate copolymer may be added immediately after mixing in the diamine, this addition is preferably delayed for at least one hour, preferably 8-16 hours, to allow the diamine to "mature" the other polymeric ingredients. This provides better control of viscosity and results in a more workable final liquid composition. Where the solvent for either the nitrocellulose or the acrylate copolymer is also a solvent for the prepolymer and the diamine, these latter ingredients need not have a separate solvent.

Alternative mixing sequences also may be employed where both the acrylate copolymer and the nitrocellulose are used to make a selectively strippable cohesive coating. A most preferred mixing sequence is the same as that in the preceding paragraph except about 10% of the nitrocellulose is held out of the composition until after addition of the diamine. After the other polymeric ingredients have "matured" with the diamine for about 10 hours, the held out portion of the nitrocellulose is added and stirred in until a uniform mixture is obtained. After this final addition of the nitrocellulose, the resulting mixture is then allowed to age further for about 24 hours before addition of the acryloid copolymer. On the other hand, where it is desirable to minimize the time required to complete preparation of a coating composition having both ingredients, the acrylate copolymer may be added ahead of the prepolymer, that is, immediately after the solvents for the nitrocellulose. For reasons that are not clear, this mixing sequence eliminates the necessity of maturing the other polymeric ingredients with the diamine before addition of the acrylate copolymer, although the mixing sequences requiring a maturing step are believed to yield more desirable products, particularly for use as nail polish. The invention can also be used to formulate strippable acrylic paints, such as latex wall paints, automotive paints, and marine paints. Such paint compositions already may contain polymers or copolymers having free acrylate groups and these polymers or copolymers may be substituted for the methyl methacrylate and butyl methacrylate copolymer described above to provide a strippable paint composition. Such strippable paints can be formulated by adding the prepolymer and the diamine to a conventional acrylic paint composition containing free (reactive) acrylate groups. The cured coating from these compositions is removed more effectively by a remover solution of toluene and isopropanol instead of a remover solution of acetone, isopropanol and water.

After all of the ingredients have been uniformly mixed, the coating composition may be stored for long periods and has an excellent shelf-life. Because the reactions are relatively slow, there is little heat of reaction so that the relatively volatile solvents remain in the composition until it is applied to a substrate as a thin coating. The coating composition can be applied as a thin, film-like coating to a substrate surface by spraying, brushing, dipping, or the like. The exact amount of solvents and/or diluents will depend on the mode of application to be used, as well as the thickness of the coating desired. For example, if the coating is to be applied by brushing, the composition should have a solids content of about 15 to 25 weight percent. However, if the composition is to be sprayed on a substrate surface, it may be desirable to reduce the solids content to about 10 weight percent or less. The resulting coating is then cured by drying in air at room temperature. Both the mixing and applying steps are also preferably carried out at room temperature (65° F. to 80° F.) and atmospheric pressure. The applied coatings dry to a non-tacky state in about 5 to 10 minutes, which is equivalent to the drying time of conventional fingernail polishes. However, for about a 10 to 24 hour period after application, the coating continues to cure and becomes tougher and more chip resistant.

Prior to adding the diamine to any of the above mixtures, other ingredients, such as color pigments, other copolymers to improve adhesion, or other plasticizer to facilitate application of the coating and/or its subsequent removal, may be added. The amount of pigment addition to the composition depends on the ultimate color desired. The amount of pigment added usually should fall within the range of 0% to 10% by weight. There also may be added dyes, thickeners, and other common additives for coatings. However, care must be taken to avoid undesirable side effects such as a shortening of pot life or unsatisfactory adhesion of the resulting film to the substrate surface. An advantage of the invention is that color pigments and other additives will not bleed out of the cured coating when contacted by organic solvents, even those for removing the coating as a cohesive film. In addition, color pigments are held within the coating so that they do not fade with aging.

Mixing of the nitrocellulose, the acrylate copolymer, the prepolymer and the other ingredients may be done by any of the usual methods, including blending by hand or standard commercial mixing units. It is critical to the invention that the prepolymer not be added prior to a major portion of the nitrocellulose and that the diamine not be added until after the prepolymer. Where the acrylate copolymer is used without nitrocellulose, this copolymer should be added ahead of the prepolymer. Although the plasticizer and a second copolymer resin may be added after the diamine, these components are preferably added before the diamine with the plasticizer being added ahead of the second copolymer resin.

The coating composition of this invention can be applied to any desired substrate surface which is not sensitive to the solvents used. Typical surfaces are fingernails, metal surfaces, wood surfaces and plastic surfaces including plexiglass. Single layer coatings are preferred although multiple layer coatings can be achieved by allowing each film layer to dry for at least 10 minutes prior to application of the next layer. The cured coatings provided by the compositions of the invention may have one or more of the following desirable characteristics: high gloss, toughness, chip-resistance, flexibility, and/or high color retention. The desirable characteristics of the strippable film after treatment with the remover solution are cohesiveness, resilience and non-smearing or bleeding of color pigments.

In order to remove the cured coating, a special remover solution is required due to the high level of interfacial adhesion between the coating and the substrate surface. The composition of this select remover solution depends on the composition of the coating. The ingredients of the remover solution are chosen so as to provide a controlled type of swelling of the polymeric network in the cured film. For example, acetone alone may swell the network and isopropanol alone may shrink the network so that the amounts of these ingredients are chosen to provide a sufficiently controlled swelling response to permit prompt removal of the coating as a cohesive film. One of the principal characteristics of the film is that it has some elastomeric properties, particularly in the swollen state created by the remover solution. For example, the cohesive film upon removal may be bent back upon itself without breaking.

Removal of the coating compositions containing the nitrocellulose or the acrylate copolymer alone or in combination with the nitrocellulose requires a remover solution of acetone, isopropanol and water. Methyl ethyl ketone (MEK) may be substituted for acetone in this remover solution. Similarly, methanol, ethanol, butanol and other alcohols may be substituted for the isopropanol. Removal of acrylic paints to which the prepolymer and diamine have been added requires a remover solution containing toluene and alcohol. To accomplish removal, it is only necessary to apply the remover solution to the dried film for about 5 to about 60 seconds, more preferably about 10 to about 30 seconds, after which the coating may be pulled from the substrate surface as a cohesive strip of film. Stripping of the film is also accomplished under normal ambient conditions.

While isopropyl alcohol is not a true solvent for nitrocellulose, when used with ethyl acetate it appears to provide a lower viscosity solution and a more workable nitrocellulose mixture. Ethyl acetate is a true solvent for nitrocellulose and appears to decrease the time required for drying the final film. Toluene is a cosolvent for nitrocellulose and for the prepolymer and also appears to reduce the viscosity of the acrylate copolymer.

Although the solvents and/or diluents are substantially removed from the composition upon drying the coating, the plasticizer remains and assists in the removal process by causing the remover solution to penetrate and be readily distributed throughout the cured coating, thus providing relatively uniform swelling and rapid loosening of the coating as a cohesive film.

One particular application of the film forming compositions of the invention is as a fingernail or toenail lacquer or polish. For this application, it is preferable that the coating composition contain both the nitrocellulose and the acrylate copolymer ingredients. In this application, the color of the fingernail polish may be changed as often as desired with a minimum of effort and without a mess since the previously applied polish may be removed as a single piece of cohesive film shortly after application of the remover solution. One advantage of such a product is the ability to provide a kit containing a limited number of different fingernail polish colors, a color chart, and a measuring container whereby a large number of desired colors can be obtained by mixing the limited number of polish colors provided in the kit. This arrangement permits the user to match the colors of the clothing chosen for a given day or evening and readily change the color for the next day or evening. This arrangement employs an eye dropper for each bottle of different fingernail polish color and the eye dropper is used to accurately transfer material from the individual bottles to a graduated measuring bottle in order to mix exact quantities of different colors according to a prescribed color chart, to thereby obtain the desired color. A composition suitable for preparing a bulb for eye droppers to be used in such an environment is described in patent application Ser. No. 521,768 filed on Aug. 8, 1983, now U.S. Pat. No. 4,464,500, the contents of which are incorporated herein by reference.

It is believed that the invention incorporates an elastomeric polymer network into a non-elastomeric polymer network. This is achieved by cross-linking and extending in a nitrocellulose and/or acrylate copolymer composition a polyurethane type molecule formed from a dimer diisocyanate prepolymer and a diamine. It is therefore an object of the invention to form polyurethane structures in situ within polymeric nitrocellulose and/or polyacrylate structures.

Without intending to be limited to any one theory or hypothesis, it is believed that the reactions between the components of the invention are as follows: the diamine first attaches itself to the nitrocellulose molecule to provide a diamine-nitrocellulose adduct with a free amine group. An NCO group of the prepolymer reacts with the acrylate copolymer to provide a prepolymer-acrylate copolymer adduct with a free NCO group. An extension reaction then proceeds with the free amine group on the diamine-nitrocellulose adduct reacting with the free NCO group on the prepolymer-acrylate copolymer adduct to produce an extremely high molecular weight material which apparently accounts for the insolubility of the cured coating and the other properties which allow this coating to be removed as one continuous piece of cohesive film. The principal film formers therefore are believed to be the nitrocellulose and/or the acrylate copolymer. It is postulated also that the diamine extends the prepolymer so as to form an ether type polyurethane within the cross-linked nitrocellulose and/or cross-link copolymer. The Santolite Resin appears to reinforce the principal film formers and to provide increased adhesion of the cured coating to a substrate.

BEST AND OTHER MODES FOR CARRYING OUT INVENTION

The proportions of the ingredients referred to as "parts" in this section of the specification are parts by weight based on 100 parts of the prepolymer unless otherwise indicated. The mixing times given below are based on mixing by hand until a substantially uniform and homogeneous mixture is obtained. After the addition of each ingredient, it is mixed thoroughly into the composition. The mixing times given are only approximations of the time required to achieve a homogeneous mass and greater mixing times may be required. Mixing of the ingredients, application of the resulting coating composition, curing of the applied coating, and removal of the cured coating as a cohesive film are all at ambient conditions of temperature (about 65° F. to 80° F.) and pressure (atmospheric).

In preferred embodiments according to the invention, about 50 to about 150 parts, preferably about 90 to about 110 parts, of nitrocellulose are first mixed with sufficient isopropyl alcohol to dissolve substantially all of the nitrocellulose (about 6 times as much alcohol as nitrocellulose). As the nitrocellulose may come as a partial solution in isopropyl alcohol, additional alcohol is added to make up the difference. Added isopropyl alcohol is mixed with the nitrocellulose for about 60 seconds. To this solution is then added about 600 to about 1,200, preferably about 800 to about 1,000, parts of ethyl acetate which is mixed in for a few seconds as a diluent. Next, about 200 to about 1,000, preferably about 500 to about 700, parts of toluene are added to the diluted nitrocellulose and mixed in for about 30 seconds. Then about 50 to about 150, preferably about 90 to about 110, parts of the prepolymer are added and mixed in for about 30 seconds. The prepolymer is preferably added as a 50% by weight solution in toluene and where this is the case, the amount of toluene added separately above is reduced by the amount of toluene to be added later with the prepolymer. There is then added to the nitrocellulose/prepolymer mixture about 8 to about 24 parts, preferably about 14 to about 18 parts, of the diamine as a dilute solution in isopropyl alcohol, preferably about 5% to about 15%, more preferably about a 10%, solution by weight. Preferably, the amount of isopropyl alcohol added earlier is reduced by the amount to be added later with the diamine. Preferably about 1.8 moles of the diamine is added for each mole of the prepolymer and the diamine is mixed in for a period of about 2 minutes.

After addition of the diamine, the resulting mixture is preferably allowed to mature for at least 1 hour, preferably at least 8 hours, and more preferably for about 8 to about 16 hours, before addition of the acrylate copolymer. This maturing time allows cross-linking of the prepolymer with the nitrocellulose and with any other polymeric ingredients, such as an adhesion promoter, and also extension of the prepolymer with the diamine, before cross-linking with the copolymer. Addition of the acrylate copolymer immediately after the diamine may adversely effect the viscosity and/or workability of the solution. Where the maturing time is sufficient to permit substantial completion of other cross-linking reactions, the viscosity of the final mixture is affected only slightly by addition of the acrylate copolymer. After maturing of the mixture with the diamine, there is added to the "matured" mixture about 50 to about 250 parts, preferably about 150 to about 225 parts, of the acrylate copolymer which is mixed in for about 1 to 2 minutes. As an alternative, these amounts of the copolymer may be added immediately after dilution of the nitrocellulose with ethyl acetate without adversely affecting the viscosity of the final solution. As another alternative, about 5 to 20%, preferably about 10% by weight of the total amount of nitrocellulose may be added after the diamine and before the acrylate copolymer.

Optionally, the composition preferably includes a plasticizer, preferably about 10 to about 60 parts, more preferably about 30 to about 50 parts, of dibutyl phthalate. The plasticizer is preferably added to the mixture along with the toluene and is mixed in therewith for about 30 seconds.

Another preferred optional ingredient is a second copolymer to improve the adhesion of the film to a substrate. Accordingly, there also may be added along with the toluene about 15 to about 75 parts, preferably about 40 to about 60 parts, of a toluene sulfonamide-formaldehyde resin, preferably either Santolite MHP or Santolite MS-80 available from Monsanto. This second copolymer resin is preferably added with the toluene and mixed in therewith for about 30 seconds.

The prepolymer is preferably from a dimer diisocyanate and triethylene glycol and is prepared as described in the paper referenced above. More preferably, about 5% to 20%, still more preferably about 10%, of the triethylene glycol is replaced by glycerol. High molecular weight dihydric alcohols may also be used in place of all or a portion of the triethylene glycol. Similarly, the alcohol component of the prepolymer may be replaced by a number of difunctional monomers having an active hydrogen in each group such as thiols, aminos, and/or carbamates.

The preferred dimer diisocyanate is based on a dimerized aliphatic fatty acid containing 36 carbon atoms. Dimers are preferred because other diisocyanates react too quickly and do not provide prepolymers having the required reactivity and flexibility to be considered as the isocyanate component of the present invention.

The diamine is preferably hexamethylene diamine (HMDA). Although other diamines may be used to extend the prepolymer and cross-link the prepolymer with the other polymeric ingredients, HMDA is preferred because of its good tensile strength and elongation characteristics. It also provides one of the lowest volume changes in response to the solvents used in the remover solution. Another diamine with similar characteristics is 1,4-cyclohexanebis(methylamine).

The acrylate copolymer preferred is available from Rohm and Haas under the tradename Acryloid B-66 and is a copolymer from methyl methacrylate and butyl methacrylate. As exemplified by the embodiments in which the prepolymer and the diamine are added to acrylic paints, there are a number of acrylates that may be employed in place of the preferred methyl methacrylate and butyl methacrylate copolymer. Such acrylates may be prepared by a copolymerizing methyl methacrylate and a diacrylate or triacrylate to yield a branched type copolymer. Similarly, the acrylate copolymer may be replaced by a copolymer from butyl methacrylate and ethyl acrylate.

In the solvent system of the coating composition, other alcohols may be substituted for isopropyl alcohol and other acetates may be substituted for ethyl acetate without adversely changing the strippable film characteristics. However, other acetates and/or alcohols may alter drying times of the applied coating due to differences in the volatility of these replacements. Similarly, in some applications, toluene could be replaced by benzene or xylene. As previously indicated, it is also possible to substitute other copolymer resins for the Santolite resins and/or other plasticizers for the dibutyl phthalate. After formulation of the coating composition, it may be packaged for sale in cans, bottles or the like. The composition has an indefinite shelf-life over which the viscosity does not increase significantly. When the composition is to be used, it may be brushed or sprayed onto a substrate surface to form a thin coating of about 1 to 3 mils in thickness. This coating dries readily in about 5 or 10 minutes to yield a non-tacky surface. Although a non-tacky condition is achieved within a short period, the coating actually continues to cure for about 10 to 24 hours into a tough, strongly adhered coating which cannot be readily removed without use of a special remover solution. The cured coating is substantially unaffected by submersion in water and in many organic solvents, including many conventional fingernail polish removers.

In order to remove the cured film, a select removal solution must be used. A preferred removal solution for the coating just described contains about 10 to about 60 parts, preferably about 30 to about 50 parts, of acetone; about 5 to about 40 parts, preferably about 10 to about 30 parts, of isopropyl alcohol; and about 5 to about 40 parts, preferably about 10 to about 30 parts, of water which preferably has been distilled; all based on 100 parts of final remover solution. The order of mixing the ingredients of the remover solution is optional and the final composition is mixed sufficiently to form a substantially uniform and homogeneous solution. The remover solution may be applied to the cured coating to be removed by any conventional means, such as brushing, spraying or dipping. Within about 10 to 40 seconds, more preferably about 20 to 30 seconds, after application of the remover solution to the cured coating, the adhesion of the coating to the substrate is loosened sufficiently so that the entire coating may be peeled away from the substrate as a cohesive film.

In selecting a specific composition in accordance with the invention for a specific application, it may be desirable to consider the following factors. As the amount of the prepolymer is decreased below the optimum range, the toughness of the coating appears to decrease, as does its cohesiveness when contacted by the remover solution. As the amount of the prepolymer is increased above the optimum range, the toughness of the coating appears to increase but the viscosity of the composition also increases and may become too great to be workable, especially where a second copolymer resin is used. The viscosity increase may be alleviated by reducing the amount of the second copolymer. As the amount of the plasticizer is reduced, the time required to remove the film after application of the remover solution appears to increase and may become excessively long. If the amount of plasticizer is increased above the optimum range, the film may soften too quickly and smear when treated with the remover solution. Higher concentrations of the plasticizer above those suggested also may adversely effect the cohesiveness of the coating and therefore its strippability. Although there is sufficient adhesion without a second copolymer to provide a useful product, omission of the second copolymer resin may significantly reduce the adhesion of the coating to a substrate. The amounts of the various solvents specified also can be adjusted as needed to yield a solution having a workable viscosity for the application desired. The preferred composition described above is suitable for use as a fingernail polish that is strippable as a cohesive film upon treatment with the remover solution. Although lacking some of the optimum characteristics desired for a fingernail polish, strippable films also may be provided by coating compositions having the same ingredients in the relative amounts specified except that either the nitrocellulose or the acrylate copolymer (but not both) is omitted. Strippable films formed by such alternative compositions also are removable by the select remover solution described above.

In other embodiments of the invention, strippable paint coatings are made by adding the prepolymer to a conventional paint composition containing one or more acrylates, mixing in the prepolymer until a substantially uniform and homogeneous mixture is obtained, and then adding the diamine and mixing in the diamine until a substantially uniform and homogeneous mixture is obtained. The amount of the prepolymer and the amount of the diamine relative to the amount of the acrylates present should fall within the same ranges as those given for the acrylate copolymer composition specified above. However, removal of the strippable film provided by such paint compositions requires a remover solution different from that for the copolymer film. The remover solution for such paint compositions preferably contains about 25 to 75 parts, preferably about 50 parts, toluene and about 25 to 75 parts, preferably about 50 parts, isopropyl alcohol, all based on 100 parts of total remover solution.

With respect to the remover solution for coatings other than acrylic paints, other ketones may substituted for the acetone and methyl or ethyl alcohol may be substituted for isopropyl alcohol. However, the preferred remover solution for these coatings contains a primary ketone solvent, and secondary alcohol solvent and a non-solvent such as water.

The following specific examples illustrate the practice of the invention, but are not intended to limit the scope thereof. As previously noted, all quantitative amounts of ingredients in the coating composition are based on weight relative to 100 parts of the prepolymer, and all quantitative amounts of the ingredients in the remover solution are based on weight relative to 100 parts of total solution, unless otherwise noted. The acrylate copolymer, the prepolymer and the diamine used in these examples are those identified above as being preferred unless otherwise indicated.

EXAMPLE I

A composition suitable for preparation of a strippable cohesive nail polish contained the following total amounts of the ingredients specified.

| INGREDIENTS | PARTS |
| --- | --- |
| Nitrocellulose | 428 |
| Dibutyl Phthalate | 40 |
| Santolite Resin MS-80 | 48 |
| Prepolymer | 100 |
| Diamine | 16 |
| Acryloid B-66 Copolymer | 200 |
| Isopropyl Alcohol | 1840 |
| Ethyl Acetate | 900 |
| Toluene | 600 |
| Xylene | 200 |
| Butyl Acetate | 12 |

The above composition was prepared by first adding 428 parts of nitrocellulose in 796 parts of isopropyl alcohol to a mixing vessel. 900 parts of isopropyl alcohol were added next and stirred for about 60 seconds. 900 parts of ethyl acetate were added next and stirred for a few seconds e.g., 5 to 10 seconds. 500 parts of toluene were added next followed by 40 parts of dibutyl phthalate and 48 parts of Santolite Resin in 12 parts of butyl acetate, and these three ingredients were stirred in for about 30 seconds. 100 parts of prepolymer in 100 parts of toluene were added next and stirred in for about 30 seconds. A dilute solution of 16 parts of diamine in 144 parts of isopropyl alcohol were added next dropwise with stirring over a period of about 2 minutes. The resulting solution at this point was allowed to mature for about 16 hours and then 200 parts of the Acryloid copolymer in 200 parts of xylene were added to the "matured" mixture. After the above composition is dried to form a film, this film is no longer soluble in either the solvent for the nitrocellulose (isopropyl alcohol and/or ethyl acetate) or in the solvent for the copolymer and prepolymer (toluene) or in the other individual solvents present, namely, xylene or butyl acetate.

As soon as the diamine is added, the solution becomes colored and the viscosity increases slowly over the next two hours, indicating that the diamine has attached itself to the nitrocellulose and/or to the prepolymer. Upon the addition of the acrylate copolymer, the viscosity increases slightly and an exothermic reaction occurs. It is believed that the acrylate reacts with some of the free NCO groups to further cross-link the total system. By adding the acrylate last, the competing reactions can be controlled to yield a workable viscosity. It is believed that several reactions proceed more or less at one time, these reactions being (1) the diamine attaches to the nitrocellulose molecule, (2) the prepolymer is extended by the diamine, and (3) the acrylate copolymer reacts with the modified prepolymer and/or the modified nitrocellulose.

A thin coating applied with the foregoing composition and dried for about 16 hours has a very high gloss and relatively good flexibility and is very tough and chip resistant. The coating has excellent adhesion to the surface of the substrate to which applied. Nevertheless, this coating is easily removed as a continuous cohesive film after about 20 seconds of contact with a remover solution containing 40 parts of acetone, 20 parts of isopropyl alcohol, and 20 parts of distilled water.

EXAMPLE II

A composition suitable for preparation of a strippable decorative coating contained the following total amounts of the ingredients specified:

| INGREDIENTS | PARTS |
| --- | --- |
| Nitrocellulose | 428 |
| Prepolymer | 100 |
| Diamine | 16 |
| Dibutyl Phthalate | 40 |
| Santolite Resin MS-80 | 48 |
| Isopropyl Alcohol | 1840 |
| Ethyl Acetate | 900 |
| Toluene | 600 |
| Butyl Acetate | 12 |

The foregoing composition was prepared by charging 428 parts of nitrocellulose in 796 parts of isopropyl alcohol to a mixing vessel and adding an additional 900 parts of isopropyl alcohol with mixing for about 60 seconds. 900 parts of ethyl acetate were added next followed by 500 parts of toluene which were mixed in for a sufficient time to obtain a homogeneous mixture of reduced viscosity (about 60 seconds). To this mixture was added 100 parts of prepolymer in 100 parts of toluene with mixing for about 60 seconds. Next were added 40 parts of dibutyl phthalate followed by 48 parts of Santolite Resin in 12 parts of butyl acetate, these ingredients being mixed in for about 30 seconds. There was then added 16 parts of diamine in 144 parts of isopropyl alcohol. After this composition was dried as a thin coating on a substrate, the coating was no longer soluble in the solvents for the prepolymer (toluene) and for the nitrocellulose (ethyl acetate) or in the other individual solvents and/or diluents used, namely, isopropyl alcohol, xylene or butyl acetate.

Upon addition of the diamine, the solution became colored and the viscosity increased slowly over the next 2 hours, indicating that the diamine had attached itself to the nitrocellulose, in addition to extending the prepolymer. It is believed that the diamine attaches one end of its molecule to the nitrocellulose chain leaving one end free to react with one NCO group from a prepolymer molecule to form an adduct. The diamine attached to a second nitrocellulose molecule reacts with the other NCO group of this adduct molecule. It is believed that this cross-linking network produces the observed viscosity change.

A coating of this composition brushed onto a substrate and allowed to dry for about 16 hours provides a relatively tough coating of high gloss. The coating was also very clear and had good adhesion to the substrate surface. Although the chip resistance and flexibility of this coating is improved over a lacquer with nitrocellulose alone, the chip resistance and flexibility is not as good as the coating provided by Example I. This coating can be loosened by applying the previously described remover solution for about 60 seconds. The network molecules of the cohesive film removed from the substrate surface appear to be only slightly swollen by the remover solution.

EXAMPLE III

A composition suitable for preparation of a strippable protective coating for a metal substrate was prepared from the following ingredients in the total amounts indicated:

| INGREDIENTS | PARTS |
| --- | --- |
| Acryloid B-66 Copolymer | 200 |
| Dibutyl Phthalate | 40 |
| Santolite Resin MS-80 | 48 |
| Prepolymer | 100 |
| Diamine | 16 |
| Isopropyl Alcohol | 1044 |
| Ethyl Acetate | 900 |
| Toluene | 600 |
| Xylene | 200 |
| Butyl Acetate | 12 |

The foregoing composition was prepared by first adding 200 parts of the acrylate copolymer in 200 parts of xylene to a mixing vessel followed by the addition of 500 parts of toluene with mixing for about 30 seconds. 900 parts of ethyl acetate and 900 parts of isopropyl alcohol were added next and mixed for about 30 seconds. 40 parts of dibutyl phthalate were added next followed by the addition of 40 parts of Santolite Resin in 12 parts of butyl acetate and these ingredients were mixed in for about 30 seconds. 100 parts of prepolymer in 100 parts of toluene were then added and mixed in for about 30 seconds. There was then added last 16 parts of diamine in 144 parts of isopropyl alcohol with vigorous mixing.

The viscosity of the mixture increased slightly after the prepolymer was added to the copolymer. When the diamine was added to the acrylate/prepolymer mixture, an immediate reaction occurred which rapidly increased the viscosity. Vigorous stirring was continued for a period of about one minute to prevent the mixture from gelling up.

Coatings from this composition were somewhat opaque and relatively soft but nevertheless were very flexible and tough. The surface appearance of this coating was flat instead of glossy. The coating had good adhesion to the substrate. About 10 seconds after application of the remover solution, the opaqueness of the coating increased and the coating was easily removed from the substrate surface as a cohesive film. The removed film no longer exhibited any solubility in toluene, which is a good solvent for the copolymer and the prepolymer prior to drying the coating composition.

EXAMPLE IV

A composition suitable for preparation of a strippable protective coating requiring a minimum of preparation time was prepared from the following ingredients in the amounts as shown:

| INGREDIENTS | PARTS |
| --- | --- |
| Nitrocellulose | 428 |
| Isopropyl Alcohol | 1840 |
| Ethyl Acetate | 900 |
| Acryloid B-66 Copolymer | 200 |
| Toluene | 600 |
| Xylene | 200 |
| Prepolymer | 100 |
| Diamine | 16 |
| Dibutyl Phthalate | 40 |
| Santolite Resin MS-80 | 48 |
| Butyl Acetate | 12 |

The above composition was prepared by first adding 428 parts of nitrocellulose in 796 parts of isopropyl alcohol to a mixing vessel. 900 parts of isopropyl alcohol were added next and stirred in for about 60 seconds. 900 parts of ethyl acetate were added next and stirred in for about 30 seconds. 200 parts of Acryloid copolymer in 200 parts of xylene were added next and stirred in for about 60 seconds. 500 parts of toluene were next added and stirred in for about 30 seconds. This addition was followed by 100 parts of prepolymer in 100 parts of toluene, which were stirred for about 30 seconds. 16 parts of diamine in 144 parts of isopropyl alcohol were next added and stirred in for about 60 seconds. 40 parts of dibutyl phthalate were added next and stirred in for about 30 seconds. Lastly, 48 parts of Santolite Resin MS-80 in 12 parts of butyl acetate were added and stirred in for about 60 seconds.

The above composition can be prepared in a minimum of time because the sequence of addition avoids the "maturing time" needed when the acrylate copolymer is added last. The coating from this composition can be stripped after drying with the following solvent mixture:

40 parts Acetone
20 parts Isopropyl Alcohol
20 parts distilled water.

EXAMPLE V

A composition suitable for preparation of a strippable nail polish having a very fast release time was prepared from the following ingredients in the amounts as shown:

| INGREDIENTS | PARTS |
| --- | --- |
| Nitrocellulose | 428 |
| Isopropyl Alcohol | 1840 |
| Ethyl Acetate | 900 |
| Acryloid B-66 Copolymer | 200 |
| Toluene | 600 |
| Xylene | 200 |
| Prepolymer | 100 |
| Diamine | 16 |
| Dibutyl Phthalate | 40 |
| Santolite Resin MS-80 | 48 |
| Butyl Acetate | 12 |

The above composition was prepared by first adding 385.2 parts of nitrocellulose in 716.8 parts of isopropyl alcohol to a mixing vessel. 900 parts of isopropyl alcohol were added next and stirred in for about 60 seconds. 900 parts of ethyl acetate were added next and stirred in for about 30 seconds. 500 parts of toluene were added next and stirred in for about 30 seconds. 40 parts of dibutyl phthalate and 48 parts of Santolite Resin MS-80 in 12 parts of butyl acetate were added together and stirred in for about 30 seconds. 100 parts of prepolymer in 100 parts of toluene were added next and stirred in for about 30 seconds. 16 parts of diamine in 144 parts isopropyl alcohol were added next and stirred in for about 60 seconds. This mixture was allowed to age for about 10 hours before adding and stirring in for about 30 seconds an additional 42.8 parts nitrocellulose in 79.2 parts isopropyl alcohol. The resulting mixture was allowed to age for about 24 hours before adding 200 parts Acryloid copolymer in 200 parts xylene.

The coating prepared from the above composition has a much faster release time (3-5 seconds) when compared to that of Example I using the same remover solution. The viscosity of the composition of Example V is also observed to be less than that of Example I. It is believed that the reduced amount of nitrocellulose/diamine adduct may account for these observations.

EXAMPLE VI

A composition suitable for preparation of a strippable acrylic paint was prepared from the following ingredients in the amounts shown:

| INGREDIENTS | PARTS |
| --- | --- |
| Acrylic Paint | 2000 |
| Prepolymer | 100 |
| Diamine | 8 |
| Toluene | 100 |
| Isopropyl Alcohol | 92 |

The above composition was prepared by first adding to a mixing vessel 2000 parts of an acrylic paint known as Delstar DAR 2058 available from PPG Industries. 100 parts of prepolymer in 100 parts of toluene were added to the mixing vessel next and stirred for about 60 seconds. Next, 8 parts of diamine in 92 parts of isopropyl alcohol were added and stirred in for about 60 seconds.

The above composition results in a coating which can be stripped after drying with a remover solution containing toluene and isopropyl alcohol in a one to one ratio by weight. This remover solution will cause solvation and smearing of a coating from the paint ingredient when used alone without the prepolymer and diamine. By comparison, the above composition was removable as a cohesive film after being in contact with the remover solution for about 30 seconds.

EXAMPLE VII

A composition suitable for preparation of a strippable protective coating was prepared from the following ingredients in the amounts as shown:

| INGREDIENTS | PARTS |
| --- | --- |
| Polymethylmethacrylate | 200 |
| Ethyl Acetate | 600 |
| Toluene | 100 |
| Prepolymer | 100 |
| CBMA | 20 |
| Acetone | 180 |

The above composition was prepared by dissolving 200 parts polymethylmethacrylate (PMMA) in 600 parts ethyl acetate. This was allowed to stand overnight to completely dissolve. 100 parts of prepolymer in 100 parts of toluene was then added to the polymer solution (PMMA) and stirred in for about 30 seconds. This was followed by adding 20 parts CBMA (diamine) in 180 parts acetone. The mixture was stirred for about 60 seconds. Films were cast and allowed to dry. When wet with a solution of 40 parts acetone, 20 parts isopropanol, and 20 parts water for a few seconds, the film could be peeled off in one continuous piece. The film was very tough and could be folded back upon itself and then creased with a thumb nail without breaking. The films were flexible and could be unfolded after creasing without breakage. This Example VI demonstrates that a strippable film can be prepared from PMMA and prepolymer in the absence of nitrocellulose.

EXAMPLE VIII

A composition suitable for preparation of a nail polish coating was prepared from the following ingredients in the amounts as shown:

| INGREDIENTS | PARTS |
| --- | --- |
| Nitrocellulose | 428 |
| Isopropyl Alcohol | 1696 |
| Ethyl Acetate | 1500 |
| Polymethylmethacrylate | 200 |
| Toluene | 600 |
| Prepolymer | 100 |
| CBMA (diamine) | 10 |
| Acetone | 90 |
| Dibutyl Phthalate | 40 |
| Santolite Resin MS-80 | 48 |
| Butyl Acetate | 12 |

The above composition was prepared by adding 428 parts of nitrocellulose in 796 parts isopropyl alcohol to a mixing vessel. 900 parts of isopropyl alcohol were added next and stirred in for about 60 seconds. 900 parts of ethyl acetate were added next and stirred in for about 30 seconds. 200 parts of PMMA dissolved in 600 parts of ethyl acetate were added next and stirred in for about 60 seconds. 100 parts of prepolymer in 100 parts toluene were next added and stirred in for about 30 seconds. 10 parts of CBMA in 90 parts of acetone, which had been previously reacted for about 10 days to form Schiff's base, were added next and stirred in for about 60 seconds. 40 parts of dibutyl phthalate and 48 parts of Santolite resin in 12 parts of butyl acetate were added next and stirred in for about 30 seconds.

The coating prepared from this composition appears to be very tough and can be removed as one continuous film when wet with a solvent mixture made from 40 parts acetone, 20 parts isopropyl alcohol, and 20 parts distilled water.

EXAMPLE IX

In the foregoing Example VIII, 10 parts of CBMA in 90 parts of isoproponal may be substituted for the Schiff's base, provided this diamine solution is added slowly dropwise with stirring over a period of about 8 to 10 minutes to prevent precipitation of polyacrylate. Examples VIII and IX demonstrate that a strippable fingernail polish can be prepared from acrylates other than the B-66 copolymer used in Examples I and III-–VII above.

In the foregoing examples, nitrocellulose was used as a 35% by weight solution in isopropyl alcohol, the acrylate copolymer was used as a 50% solution in xylene, the prepolymer was used as a 50% solution in toluene, the diamine was used as a 10% solution in isopropyl alcohol, and the Santolite Resin was used as an 80% solution in butyl acetate. All of these percentages are by weight and are equivalent to the relative parts given in the examples.

What is claimed is:

1. A composition suitable for preparation of a strippable coating, said composition comprising:
   an acrylate copolymer;
   a mixing solvent comprising a solvent for said acrylate copolymer;
   a prepolymer from a dimer diisocyanate and a difunctional monomer with an active hydrogen in each group; and,
   a diamine;
   said copolymer, said prepolymer and said diamine being mixed in the presence of said mixing solvent so as to provide said composition and said composition when dried as a coating on a substrate providing a coating which is not removable from said substrate by said mixing solvent but instead is removable as a cohesive film by a select solvent other than said mixing solvent.

2. A composition according to claim 1 in which said difunctional monomer comprises a dihydric and/or polyhydric alcohol.

3. A composition according to claim 2 in which said alcohol comprises a dihydric alcohol and said dimer diisocyanate comprises an aliphatic diisocyanate based on a dimerized fatty acid containing 36 carbon atoms.

4. A composition according to claim 3 in which said alcohol comprises triethylene glycol.

5. A composition according to claim 4 in which said acrylate is a copolymer from methyl methacrylate and butyl methacrylate.

6. A composition according to claim 5 in which said mixing solvent further comprises toluene as a solvent for said acrylate copolymer.

7. A composition according to claim 1 which further comprises nitrocellulose and in which said mixing solvent further comprises a solvent for said nitrocellulose.

8. A composition according to claim 7 in which said nitrocellulose solvent comprises isopropyl alcohol and ethyl acetate.

9. A composition according to claim 7 in which said diamine comprises 1,4-cyclohexanebis(methylamine).

10. A composition according to claim 9 in which said mixing solvent further comprises toluene as a solvent for said acrylate polymer, and in which said nitrocellulose solvent comprises isopropyl alcohol and ethyl acetate.

11. A composition according to claim 3 which comprises about 50 to 150 parts of nitrocellulose, about 50 to 150 parts of said acrylate polymer, about 50 to 150 parts of said prepolymer, and about 8 to 24 parts of said diamine, said parts being parts by weight based on 100 parts of said prepolymer.

12. A composition according to claim 1 which further contains a second copolymer to increase adhesion between said coating and a substrate.

13. A composition according to claim 11 which further comprises about 15 to 75 parts of a second copolymer from sulfonamide and formaldehyde.

14. A composition according to claim 1 which further contains a plasticizer.

15. A composition according to claim 13 which further contains as a plasticizer about 10 to 60 parts of dibutyl phthalate.

16. A method of preparing a composition suitable for providing a strippable coating on a substrate surface comprising:
   uniformly mixing an acrylate copolymer from methyl methacrylate and butyl methacrylate with a mixing solvent comprising a solvent for said copolymer;
   uniformly mixing a prepolymer with said copolymer, said prepolymer being from a dimer diisocyanate and a difunctional monomer having an active hydrogen in each group; and,
   uniformly mixing a diamine with said prepolymer and said copolymer in the presence of said mixing solvent so as to provide said composition, said composition when dried as a coating on a substrate surface providing a coating which is not removable from said substrate surface by mixing solvent but instead is removable as a cohesive film by a select solvent other than said mixing solvent.

17. A method of removing a strippable coating provided by applying to a substrate surface and thereafter drying the composition prepared according to claim 16, said method of removal comprising applying to said dried coating a remover solution comprised of acetone, isopropyl alcohol and water so as to loosen said strippable coating relative to said substrate surface, and stripping said loosened coating from said substrate surface as a cohesive film.

18. A method of removal according to claim 17 in which said remover solution comprises about 10 to about 60 parts of acetone, about 5 to about 40 parts of isopropyl alcohol, and about 5 to about 40 parts of water.

19. A method of preparing a composition suitable for providing a strippable coating on a substrate surface comprising:
   uniformly mixing nitrocellulose with a mixing solvent comprising a solvent for said nitrocellulose;
   uniformly mixing a prepolymer with said nitrocellulose, said prepolymer being from a dimer diisocyanate and difunctional monomer having an active hydrogen in each group;
   uniformly mixing a diamine with said nitrocellulose and said prepolymer; and,
   uniformly mixing an acrylate copolymer from methyl methacrylate and butyl methacrylate with said nitrocellulose, said prepolymer and said diamine so as to provide said composition, said composition when dried as a coating on a substrate surface providing a coating which is not removable from said substrate surface by said mixing solvent but instead is removable as a cohesive film by a select solvent other than said mixing solvent.

20. A method of removing a strippable coating provided by applying to a substrate surface and thereafter drying the composition prepared according to claim 19, said method of removal comprising applying to said dried coating a remover solution comprised of acetone, isopropyl alcohol and water so as to loosen said strippable coating relative to said substrate surface, and stripping said loosened coating from said substrate surface as a cohesive film.

21. A method according to claim 20 in which said remover solution comprises about 10 to about 60 parts of acetone, about 5 to about 40 parts of isopropyl alcohol, and about 5 to about 40 parts of water.

22. An article of manufacture comprising a substrate coated with a strippable coating provided by applying to a surface of said substrate and thereafter drying the composition according to claim 1, the difunctional monomer of said composition comprising a dihydric or polyhydric alcohol.

23. An article according to claim 22 in which said acrylate polymer is a copolymer from methyl methacrylate and butyl methacrylate, said alcohol comprises triethylene glycol, and said dimer diisocyanate comprises an aliphatic diisocyanate based on a dimerized fatty acid containing 36 carbon atoms.

24. An article according to claim 22 in which said composition further comprises nitrocellulose.

25. An article according to claim 24 in which said composition further comprises a second copolymer from a sulfonamide and formaldehyde.

26. An article according to claim 24 in which said composition further comprises a plasticizer.

27. An article according to claim 26 in which said plasticizer includes dibutyl phthalate.

28. An article according to claim 24 in which said alcohol further comprises a glycerol.

29. An article according to claim 24 in which said composition further comprises a color pigment.

30. An article according to claim 24 in which said diamine comprises 1,4-cyclohexanebis(methylamine).

31. A composition suitable for preparation of a strippable coating selectively removable from a substrate as a cohesive film, said composition comprising:
nitrocellulose;
a mixing solvent comprising a solvent for said nitrocellulose;
a prepolymer from a dimer diisocyanate and a dihydric or polyhydric alcohol; and,
a diamine;
said nitrocellulose, said prepolymer and said diamine being mixed in the presence of said mixing solvent so as to provide said composition, and said composition when dried as a coating on a substrate providing a coating which is not removable from said substrate by said mixing solvent but instead is removable as a cohesive film by a select solvent other than said mixing solvent.

32. A composition according to claim 31 in which said dimer diisocyanate comprises an aliphatic diisocyanate based on a dimerized fatty acid containing 36 carbon atoms.

33. A composition according to claim 32 in which said alcohol comprises a mixture of triethylene glycol and glycerol.

34. A composition according to claim 32 which further comprises an acrylate copolymer.

35. A composition according to claim 34 in which said acrylate copolymer is from methyl methacrylate and butyl methacrylate.

36. A composition according to claim 35 which further comprises a plasticizer.

37. A composition according to claim 36 in which said plasticizer comprises dibutyl phthalate.

38. A composition according to claim 36 in which said composition further comprises a second copolymer from a sulfonamide and formaldehyde.

39. A composition according to claim 34 in which said composition further comprises a color pigment and said composition is suitable for use as a nail polish.

* * * * *